(12) United States Patent
Chen et al.

(10) Patent No.: US 6,391,643 B1
(45) Date of Patent: May 21, 2002

(54) KIT AND METHOD FOR QUALITY CONTROL TESTING OF AN IONTOPHORETIC SAMPLING SYSTEM

(75) Inventors: Qiang Chen, Sunnyvale; David M. Liu, Los Altos; Brian S. Kersten, San Mateo; Christine M. Wu, Fremont, all of CA (US)

(73) Assignee: Cygnus, Inc., Redwood City, CA (US)

( * ) Notice: Subject to any disclaimer, the term of this patent is extended or adjusted under 35 U.S.C. 154(b) by 0 days.

(21) Appl. No.: 09/428,587

(22) Filed: Oct. 27, 1999

Related U.S. Application Data
(60) Provisional application No. 60/106,024, filed on Oct. 28, 1998.

(51) Int. Cl.$^7$ ................................................ G01N 31/00
(52) U.S. Cl. ........................ 436/14; 436/8; 422/61; 435/14; 73/1.01; 73/1.02; 600/347; 600/365; 604/20
(58) Field of Search ............................... 436/8, 14, 149, 436/150, 151; 422/61, 68.1, 82.01, 82.03; 702/19, 22, 23; 73/1.01, 1.02; 604/20; 600/345, 346, 347, 365; 607/115, 149

(56) References Cited

U.S. PATENT DOCUMENTS

| | | | |
|---|---|---|---|
| 5,139,023 A | 8/1992 | Stanley et al. | 600/368 |
| 5,279,543 A | 1/1994 | Glikfeld et al. | 604/20 |
| 5,362,307 A | 11/1994 | Guy et al. | 604/20 |
| 5,636,632 A | 6/1997 | Bommannan et al. | 600/576 |
| 5,730,714 A | 3/1998 | Guy et al. | 604/20 |
| 5,735,273 A | 4/1998 | Kurnik et al. | 600/345 |
| 5,771,890 A | 6/1998 | Tamada | 600/347 |
| 5,827,183 A | 10/1998 | Kurnik et al. | 600/345 |
| 5,954,685 A | 9/1999 | Tierney | 604/20 |
| 5,989,409 A | 11/1999 | Kurnik et al. | 205/792 |
| 6,083,196 A * | 7/2000 | Trautman et al. | 604/46 |
| 6,144,869 A * | 11/2000 | Berner et al. | 600/347 |
| 6,180,416 B1 * | 1/2001 | Kurnik et al. | 436/518 |
| D438,807 S | 3/2001 | Liu | D10/81 |
| 6,233,471 B1 * | 5/2001 | Berner et al. | 600/345 |
| 6,272,364 B1 * | 8/2001 | Kurnik | 600/345 |

FOREIGN PATENT DOCUMENTS

| | | |
|---|---|---|
| EP | 0 240 593 A1 | 10/1987 |
| EP | 942 278 A2 | 9/1999 |
| WO | WO 95/02357 | 1/1995 |
| WO | WO 96/00109 | 1/1996 |
| WO | WO 96/00110 | 1/1996 |
| WO | WO 97/02811 | 1/1997 |
| WO | WO 97/10356 | 3/1997 |
| WO | WO 97/10499 | 3/1997 |
| WO | WO 97/24059 | 7/1997 |
| WO | WO 98/42252 | 10/1998 |
| WO | WO 99/58050 | 11/1999 |
| WO | WO 99/58051 | 11/1999 |
| WO | WO 99/58190 | 11/1999 |
| WO | WO 99/58973 | 11/1999 |

* cited by examiner

*Primary Examiner*—Maureen M. Wallenhorst
(74) *Attorney, Agent, or Firm*—Barbara G. McClung; Robins & Pasternak LLP (57) ABSTRACT

An automated system for continual transdermal extraction of analytes present in a biological system is described. The system optionally uses reverse iontophoresis to carry out the continual transdermal extraction of the analytes. The present invention describes quality control test kits, and methods of use thereof, for testing the ability of the system to provide reliable, effective, and accurate determination of analyte concentration.

15 Claims, 6 Drawing Sheets

KIT AND METHOD FOR QUALITY CONTROL TESTING OF AN IONTOPHORETIC SAMPLING SYSTEM

CROSS REFERENCE TO RELATED APPLICATION

This application is related to provisional patent application Serial No. 60/106,024, filed Oct. 28, 1998, from which priority is claimed under 35 USC §119 (e) (1) and which is incorporated herein by reference in its entirety.

TECHNICAL FIELD OF THE INVENTION

This invention relates generally to a reliable an effective method for determining that and iontophoretic sampling system can provide a predicable response to a known concentration of an analyte of interest. The invention also relates to kits useful in the practice of the method of the present invention. In one embodiment, the analyte of interest is glucose.

BACKGROUND OF THE INVENTION

A number of diagnostic tests are routinely performed on humans to evaluate the amount or existence of substances present in blood or other body fluids. These diagnostic tests typically rely on physiological fluid samples removed from a subject, either using a syringe or by pricking the skin. One particular diagnostic test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise.

Conventional blood glucose monitoring methods generally require the drawing of a blood sample (e.g., by fingerprick) for each test, and a determination of the glucose level using an instrument that reads glucose concentrations by electrochemical or calorimetric methods. Type I diabetics must obtain several fingerprick blood glucose measurements each day in order to maintain tight glycemic control. However, the pain and inconvenience associated with this blood sampling, along with the fear of hypoglycemia, has lead to poor patient compliance, despite strong evidence that tight control dramatically reduces long-term diabetic complications. In fact, these considerations can often lead to an abatement of the monitoring process by the diabetic.

Recently, various methods for determining the concentration of blood analytes without drawing blood have been developed. For example, U.S. Pat. No. 5,267,152 to Yang et al. describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al.

U.S. Pat. No. 5,139,023 to Stanley describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder.

In addition, U.S. Pat. No. 5,279,543 to Glikfeld describes the use of iontophoresis to noninvasively sample a substance through skin into a receptacle on the skin surface. Glikfeld suggests that this sampling procedure can be coupled with a glucose-specific biosensor or glucose-specific electrodes in order to monitor blood glucose. Finally, International Publication No. WO 96/00110 to Tamada describes an iontophoretic apparatus for transdermal monitoring of a target substance, where an iontophoretic electrode is used to move an analyte into a collection reservoir and a biosensor is used to detect the target analyte present in the reservoir.

SUMMARY OF THE INVENTION

The present invention relates generally to a reliable and effective method for determining that an iontophoretic sampling system can provide a predictable response to a known concentration of an analyte of interest. In a preferred embodiment, the analyte of interest is glucose.

In one aspect, the invention includes a kit for testing the efficacy of an iontophoretic sampling system, where the iontophoretic sampling system has first and second surfaces and the first surface has a reservoir containing an ionically conductive medium, as well as, an enzyme capable of reacting with glucose to produce hydrogen peroxide. The kit comprises a cover and a container of glucose solution. The cover has a shape that encloses the reservoir. Further, the cover has a top surface, retaining sides, and a bottom surface where the bottom surface defines an opening such that when the bottom surface of the cover is in contact with the first surface of the iontophoretic sampling system the first surface completes a bottom for the cover and creates an enclosed space. The retaining sides are appropriately formed and may be, for example, be angular or curved. Further, the top of the cover defines an opening through which a solution can be introduced. In addition, the top of the cover may have a slit or other openings to allow for elimination of air bubbles. Such a slit is generally centrally located in the top of the cover. The kit also includes a container holding a stable solution of glucose, where the glucose solution has a volume sufficient to at least cover the ionically conductive medium, and preferably fill the enclosed space.

The cover of the present invention may be formed from materials including, but not limited to, polystyrene, polycarbonate, nylon, and polyester glycol.

The kit may further comprise an adhesive strip effective to seal the opening and the slit, where adhesion of the strip to the cover prevents glucose solution from leaking out.

Figure 5A:
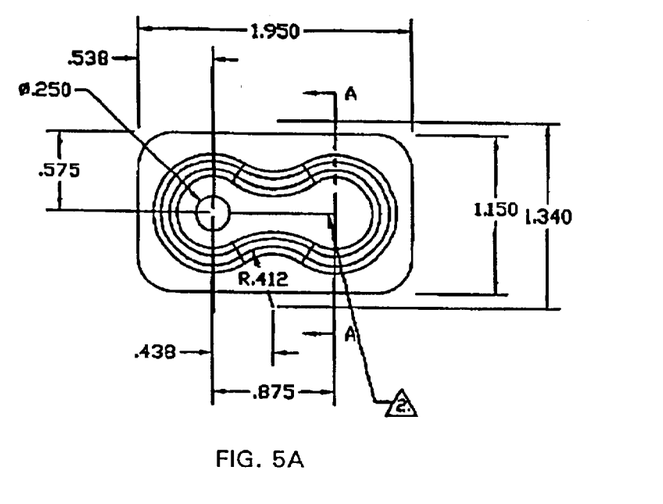
FIGS. 5A, 5B, and 5C present three different schematic views of one embodiment of the sampling system cover of the present invention.
Figure 5B:
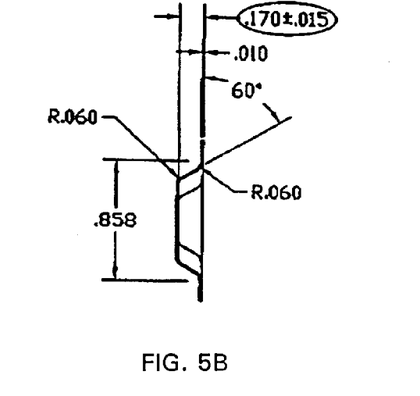
Figure 5C:
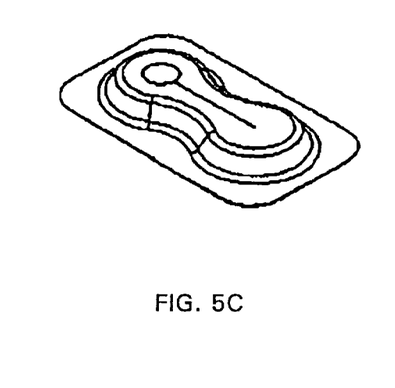

One embodiment of the cover of the present invention is shown in FIGS. 5A, 5B, and 5C. FIG. 5C shows an exemplary flanged surface. Typically the first surface has an adhesive on it, however, the bottom surface of the cover may have an adhesive distributed on the surface.

The kit can include instructions for use.

Figure 6:
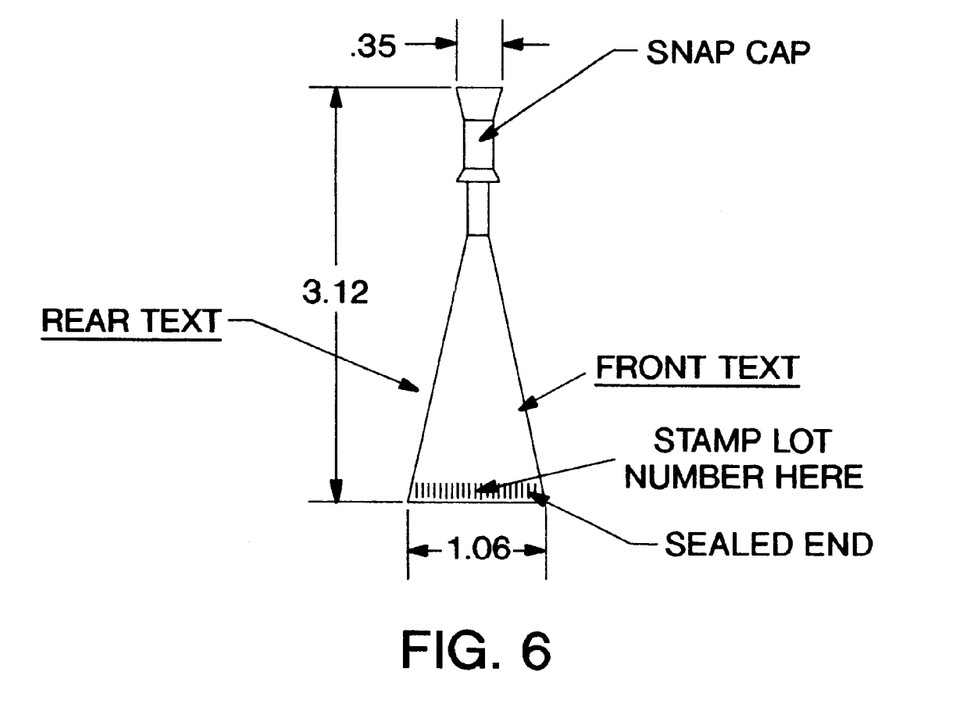
FIG. 6 presents a schematic view of one embodiment of the glucose test-solution container of the present invention.

In one embodiment of the invention, the glucose solution in the test kit has a concentration of 100 $\mu$M. The solution may also contain a preservative. Such preservatives include, but are not limited to, sodium benzoate, methyl propyl isoparaben, sodium azide, and sodium nipagin. In a preferred embodiment, the preservative is sodium benzoate at 0.2% (w/w). An exemplary snap-top container for the glucose solution is shown in FIG. 6.

The present invention further includes, a method of testing an iontophoretic sampling system's ability to determine the sensitivity of the sampling system relative to a concentration of glucose in a glucose solution, where the iontophoretic sampling system has first and second surfaces and the first surface has a reservoir containing an ionically conductive medium and an enzyme capable of reacting with glucose to produce hydrogen peroxide. The method includes, but is not necessarily limited to, the following steps:

(a) connecting the iontophoretic sampling system to appropriate sampling means;
(b) placing a cover, described above, on the iontophoretic sampling system,
(c) introducing a solution of glucose through the opening, where the glucose solution has a volume sufficient to at least cover said ionically conductive medium; and
(d) testing the iontophoretic sampling system's sensitivity relative to a concentration of glucose in a glucose solution.

The invention also includes a method of testing an iontophoretic sampling system's ability to determine the concentration of glucose in a glucose solution, following essentially the same steps as just described.

Further, in another aspect the invention includes a method of testing an iontophoretic sampling system's ability to determine that an iontophoretic sampling system can provide a predictable response to a known concentration of glucose in a glucose solution. This method follows essentially the same step outlined above.

Additional objects, advantages and novel features of the invention will be set forth in part in the description which follows, and in part will become apparent to those skilled in the art upon examination of the following, or may be learned by practice of the invention.

BRIEF DESCRIPTION OF TEE DRAWINGS

FIG. 3 is a representation of one embodiment of a bimodal electrode design. The figure presents an overhead and schematic view of the electrode assembly 33. In the figure, the bimodal electrode is shown at 30 and can be, for example, a Ag/AgCl iontophoretic/counter electrode. The sensing or is working electrode (made from, for example, platinum) is shown at 31. The reference electrode is shown at 32 and can be, for example, a Ag/AgCl electrode. The components are mounted on a suitable nonconductive substrate 34, for example, plastic or ceramic. The conductive leads 37 leading to the connection pad 35 are covered by a second nonconductive piece 36 of similar or different material. In this example of such an electrode the working electrode area is approximately 1.35 $cm^2$. The dashed line in FIG. 3 represents the plane of the cross-sectional schematic view presented in FIG. 4.

DETAILED DESCRIPTION OF THE INVENTION

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a binder" includes a mixture of two or more such binders, reference to "an analyte" includes mixtures of analytes, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

1. Definitions

In describing and claiming the present invention, the following terminology will be used in accordance with the definitions set out below.

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," or "collection reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 20, 1997); and WO 97/43962 (published Nov. 27, 1997). Laser devices use a small laser beam to burn a hole through the upper layer of the patient's skin (see, e.g., Jacques et al. (1978) *J. Invest. Dermatology* 88:88–93). Examples of invasive sampling techniques include traditional needle and syringe or vacuum sample tube devices.

The term "collection reservoir" is used to describe any suitable containment means for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place. Such collection reservoirs can be in the form of a hydrogel (for example, in the form of a disk or pad). Hydrogels are typically referred to as "collection inserts." Other suitable collection reservoirs include, but are not limited to, tubes, vials, capillary collection devices, cannulas, and miniaturized etched, ablated or molded flow paths.

A "housing" for the sampling system can further include suitable electronics (e.g., microprocessor, memory, display and other circuit components) and power sources for operating the sampling system in an automatic fashion.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means. As used herein, the term "continual measurements" intends a series of two or more measurements obtained from a particular biological system, which measurements are obtained using a single device maintained in operative contact with the biological system over the time period in which the series of measurements is obtained. The term thus includes continuous measurements.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike, et al., (1967) *Nature* 214:986–988), and other amperometric, coulometric, or potentiometric electrochemical devices.

Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (*Analytical Chemistry* 67 (24), 4594–4599, 1995).

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanocrylate adhesives, epoxies, contact adhesives, and heat sensitive adhesives.

A "collection assembly", as used herein, refers to structures comprised of several layers, where the assembly includes at least one collection insert, for example a hydrogel. An example of a collection assembly of the present invention is a mask layer, collection inserts, and a retaining layer where the layers are held in appropriate, functional relationship to each other but are not necessarily a laminate, i.e., the layers may not be bonded together. The layers may, for example, be held together by interlocking geometry or friction.

An "autosensor assembly", as used herein, refers to structures generally comprising a mask layer, collection inserts, a retaining layer, an electrode assembly, and a support tray. The autosensor assembly may also include liners. The layers of the assembly are held in appropriate, functional relationship to each other.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode.

"Substantially planar" as used herein, includes a planar surface that contacts a slightly curved surface, for example, a forearm or upper arm of a subject. A "substantially planar" surface is, for example, a surface having a shape to which skin can conform, i.e., contacting contact between the skin and the surface.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

2. Exemplary Embodiments of Sampling Systems

An exemplary method and apparatus for sampling small amounts of an analyte via transdermal methods is described below. The method and apparatus are used to detect and/or quantify the concentration of a target analyte present in a biological system. This sampling is carried out in a continual manner, and quantification is possible even when the target analyte is extracted in sub-millimolar concentrations. Although the method and apparatus are broadly applicable to sampling any chemical analyte and/or substance, the sampling system is expressly exemplified for use in transdermal sampling and quantifying or qualifying glucose or a glucose metabolite.

Accordingly, in one aspect, an automatic sampling system is used to monitor levels of glucose in a biological system. The method can be practiced using a sampling system (device) which transdermally extracts glucose from the system, in this case, an animal subject. Transdermal extraction is carried out by applying an electrical current or ultrasonic radiation to a tissue surface at a collection site. The electrical current or ultrasonic radiation is used to extract small amounts of glucose from the subject into a collection reservoir. The collection reservoir is in contact with a biosensor which provides for measurement of glucose concentration in the subject.

In the practice, a collection reservoir is contacted with a tissue surface, for example, on the stratum corneum of a patient's skin. An electrical or ultrasonic force is then applied to the tissue surface in order to extract glucose from the tissue into the collection reservoir. Extraction is carried out continually over a period of about 1–24 hours, or longer. The collection reservoir is analyzed, at least periodically, to measure glucose concentration therein. The measured value correlates with the subject's blood glucose level.

More particularly, one or more collection reservoirs are placed in contact with a tissue surface on a subject. The collection reservoirs are also contacted with an electrode which generates a current (for reverse iontophoretic extraction) or with a source of ultrasonic radiation such as a transducer (for sonophoretic extraction) sufficient to extract glucose from the tissue into the collection reservoir.

The collection reservoir contains an ionically conductive liquid or liquid-containing medium. The conductive medium is preferably a hydrogel which can contain ionic substances in an amount sufficient to produce high ionic conductivity. The hydrogel is formed from a solid material (solute) which, when combined with water, forms a gel by the formation of a structure which holds water including interconnected cells and/or network structure formed by the solute. The solute may be a naturally occurring material such as the solute of natural gelatin which includes a mixture of proteins obtained by the hydrolysis of collagen by boiling skin, ligaments, tendons and the like. However, the solute or gel forming material is more preferably a polymer material (including, but not limited to, polyethylene oxide, polyvinyl alcohol, polyacrylic acid, polyacrylamidomethylpropanesulfonate and copolymers thereof, and polyvinyl pyrrolidone) present in an amount in the range of more than 0.5% and less than 40% by weight, preferably 8 to 12% by weight when a humectant is also added, and preferably about 15 to 20% by weight when no humectant is added. Additional materials may be added to the hydrogel, including, without limitation, electrolyte (e.g., a salt), buffer, tackifier, humectant, biocides, preservatives and enzyme stabilizers. Suitable hydrogel formulations are described in International Publication Nos. WO 97/02811, published Jan. 30, 1997, and WO 96/00110, published Jan. 4, 1996, each of which publications are incorporated herein by reference in their entireties.

Since the sampling system must be operated at very low (electrochemical) background noise levels, the collection reservoir must contain an ionically conductive medium that does not include significant electrochemically sensitive components and/or contaminants. Thus, the preferred hydrogel composition described hereinabove is formulated using a judicious selection of materials and reagents which do not add significant amounts of electrochemical contaminants to the final composition.

Figure 1:
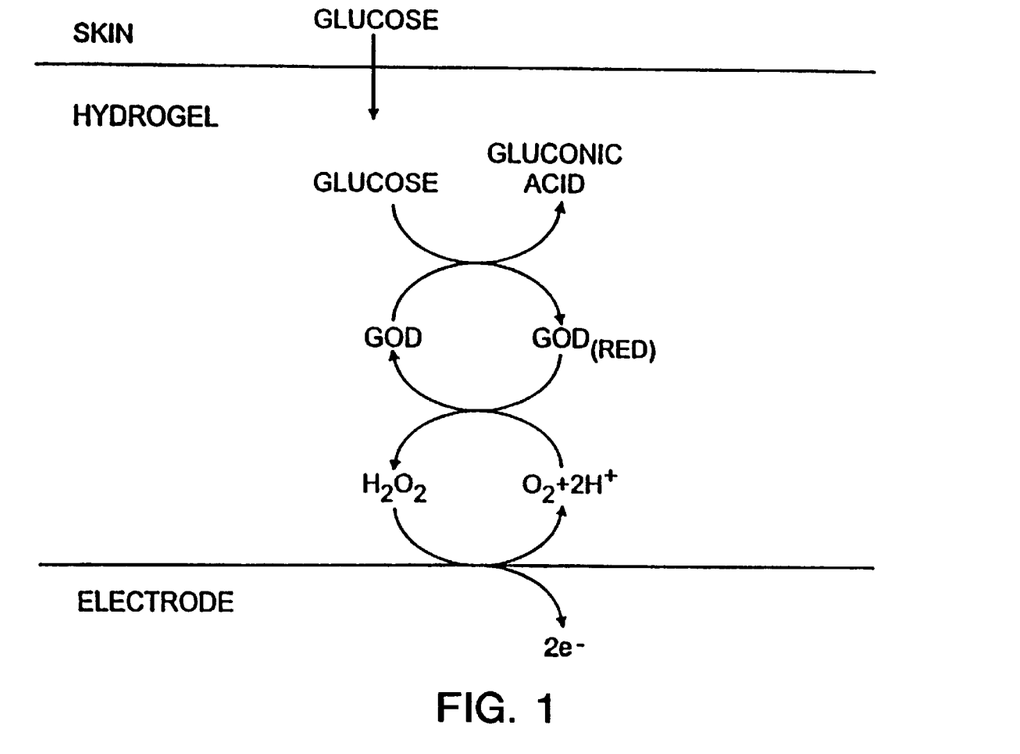
FIG. 1 is a schematic representation of the reaction which glucose oxidase (GOx) catalyzes to obtain gluconic acid and hydrogen peroxide, and result in the generation of a current.

In order to facilitate detection of the analyte, an enzyme is disposed within the one or more collection reservoirs. The enzyme is capable of catalyzing a reaction with the extracted analyte (in this case glucose) to the extent that a product of this reaction can be sensed, e.g., can be detected electrochemically from the generation of a current which current is detectable and proportional to the amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device (see FIG. 1). Glucose oxidase (GOx) is readily available commercially and has well known catalytic characteristics. However, other enzymes can also be used, so long as they specifically catalyze a reaction with an analyte, or derivative thereof (or substance of interest), to generate a detectable product in proportion to the amount of analyte so reacted.

In like manner, a number of other analyte-specific enzyme systems can be used in the sampling system, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

The biosensor electrode must be able to detect the glucose analyte extracted into the one or more collection reservoirs even when present at nominal concentration levels. In this regard, conventional electrochemical detection systems which utilize glucose oxidase (GOx) to specifically convert glucose to hydrogen peroxide, and then detect with an appropriate electrode, are only capable of detecting the analyte when present in a sample in at least mM concentrations. In contrast, the sampling system allows sampling and detection of small amounts of analyte from the subject, wherein the analyte is detected at concentrations on the order of 2 to 4 orders of magnitude lower (e.g., $\mu$M concentration in the reservoir) than presently detectable with conventional systems.

Accordingly, the biosensor electrode must exhibit substantially reduced background current relative to prior such electrodes. In one particularly preferred embodiment, an electrode is provided which contains platinum (Pt) and graphite dispersed within a polymer matrix. The electrode exhibits the following features, each of which are essential to the effective operation of the biosensor: background current in the electrode due to changes in the Pt oxidation state and electrochemically sensitive contaminants in the electrode formulation is substantially reduced; and catalytic activity (e.g., nonelectrochemical hydrogen peroxide decomposition) by the Pt in the electrode is reduced.

The Pt-containing electrode is configured to provide a geometric surface area of about 0.1 to 3 $cm^2$, preferably about 0.5 to 2 cm$^2$, and more preferably about 1 cm$^2$. This particular configuration is scaled in proportion to the collection area of the collection reservoir used in the sampling system, throughout which the extracted analyte and/or its reaction products will be present. The electrode is specially formulated to provide a high signal-to-noise ratio (S/N ratio) for this geometric surface area not heretofore available with prior Pt-containing electrodes. For example, a Pt-containing electrode constructed for use in the sampling system and having a geometric area of about 1 cm$^2$ preferably has a background current on the order of about 20 nA or less (when measured with buffer solution at 0.6V), and has high sensitivity (e.g., at least about 60 nA/$\mu$M of H$_2$O$_2$ in buffer at 0.6V). In like manner, an electrode having a geometric area of about 0.1 cm$^2$ preferably has a background current of about 2 nA or less and sensitivity of at least about 6 nA/$\mu$M of H$_2$O$_2$; and an electrode having a geometric area of about 3 cm$^2$ preferably has a background current of about 60 nA or less and sensitivity of at least about 180 nA/$\mu$M of H$_2$O$_2$, both as measured in buffer at 0.6V. These features provide for a high S/N ratio, for example a S/N ratio of about 3 or greater. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times.

The Pt powder used to formulate the electrode composition is also substantially free from impurities, and the Pt/graphite powders are evenly distributed within the polymer matrix using, for example, co-milling or sequential milling of the Pt and graphite. Alternatively, prior to incorporation into the polymer matrix, the Pt can be sputtered onto the graphite powder, colloidal Pt can be precipitated onto the graphite powder (see, e.g., U.K. patent application number GB 2,221,300, published Jan. 31, 1990, and references cited therein), or the Pt can be adsorbed onto the graphite powder to provide an even distribution of Pt in contact with the conductive graphite. In order to improve the S/N ratio of the electrode, the Pt content in the electrode is lower relative to prior Pt or Pt-based electrodes. In a preferred embodiment, the overall Pt content is about 3–7% by weight. Although decreasing the overall amount of Pt may reduce the sensitivity of the electrode, the inventors have found that an even greater reduction in background noise is also achieved, resulting in a net improvement in signal-to-noise quality.

The Pt/graphite matrix is supported by a suitable binder, such as an electrochemically inert polymer or resin binder, which is selected for good adhesion and suitable coating integrity. The binder is also selected for high purity, and for absence of components with electrochemical background. In this manner, no electrochemically sensitive contaminants are introduced into the electrode composition by way of the binder. A large number of suitable such binders are known in the art and are commercially available, including, without limitation, vinyl, acrylic, epoxy, phenoxy and polyester polymers, provided that the binder or binders selected for the formulation are adequately free of electroactive impurities.

The Pt/graphite biosensor electrodes formulated above exhibit reduced catalytic activity (e.g., passive or nonelectrochemical hydrogen peroxide degradation) relative to prior Pt-based electrode systems, and thus have substantially improved signal-to-noise quality. In preferred Pt/graphite electrode compositions, the biosensor exhibits about 10–25% passive hydrogen peroxide degradation.

Once formulated, the electrode composition is affixed to a suitable nonconductive surface which may be any rigid or flexible material having appropriate insulating and/or dielectric properties. The electrode composition can be affixed to the surface in any suitable pattern or geometry, and can be applied using various thin film techniques, such as sputtering, evaporation, vapor phase deposition, or the like; or using various thick film techniques, such as film laminating, electroplating, or the like. Alternatively, the composition can be applied using screen printing, pad printing, inkjet methods, transfer roll printing, or similar techniques. Preferably, the electrode is applied using a low temperature screen print onto a polymeric substrate. The screening can be carried out using a suitable mesh, ranging from about 100–400 mesh.

As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted by an associated system controller to provide a glucose concentration value for display. In particular embodiments, the detected current can be correlated with the subject's blood glucose concentration so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system. In this manner, measurements obtained by the sampling system can be correlated to actual values using known statistical techniques.

In one preferred embodiment, the automatic sampling system transdermally extracts the sample in a continual manner over the course of a 1–24 hour period, or longer, using reverse iontophoresis. More particularly, the collection reservoir contains an ionically conductive medium, preferably the hydrogel medium described hereinabove. A first iontophoresis electrode is contacted with the collection reservoir (which is in contact with a target tissue surface), and a second iontophoresis electrode is contacted with either a second collection reservoir in contact with the tissue surface, or some other tonically conductive medium in contact with the tissue. A power source provides an electric potential between the two electrodes to perform reverse iontophoresis in a manner known in the art. As discussed above, the biosensor selected to detect the presence, and possibly the level, of the target analyte (glucose) within a reservoir is also in contact with the reservoir.

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in International Publication No. WO 96/00110, published Jan. 4, 1996.

As an example, to extract glucose, the applied electrical current density on the skin or tissue is preferably in the range of about 0.01 to about 2 mA/cm$^2$. In a preferred embodiment, in order to facilitate the extraction of glucose, electrical energy is applied to the electrodes, and the polarity of the electrodes is alternated at a rate of about one switch every 7.5 minutes (for a 15 minute extraction period), so that each electrode is alternately a cathode or an anode. The polarity switching can be manual or automatic.

Any suitable iontophoretic electrode system can be employed, however it is preferred that a silver/silver chloride (Ag/AgCl) electrode system is used. The iontophoretic electrodes are formulated using two critical performance parameters: (1) the electrodes are capable of continual operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes.

Figure 3:
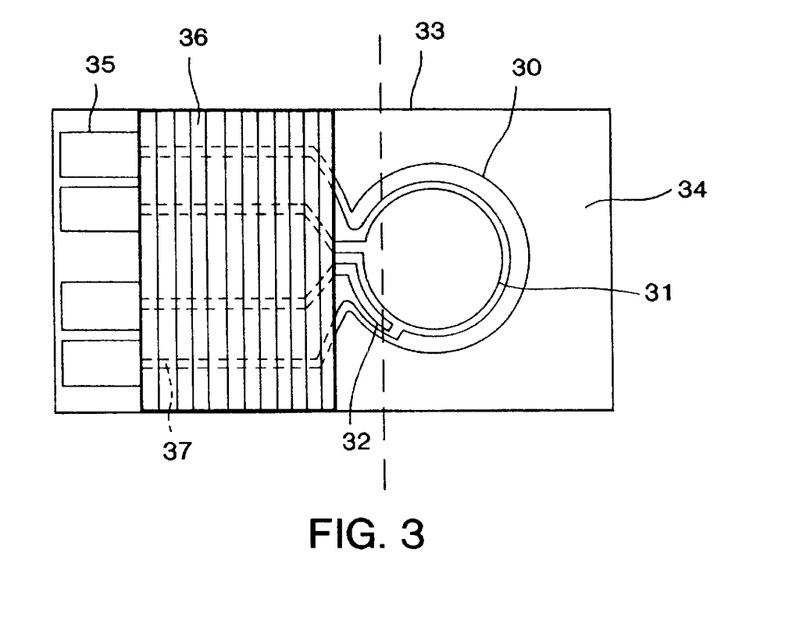
Figure 4:
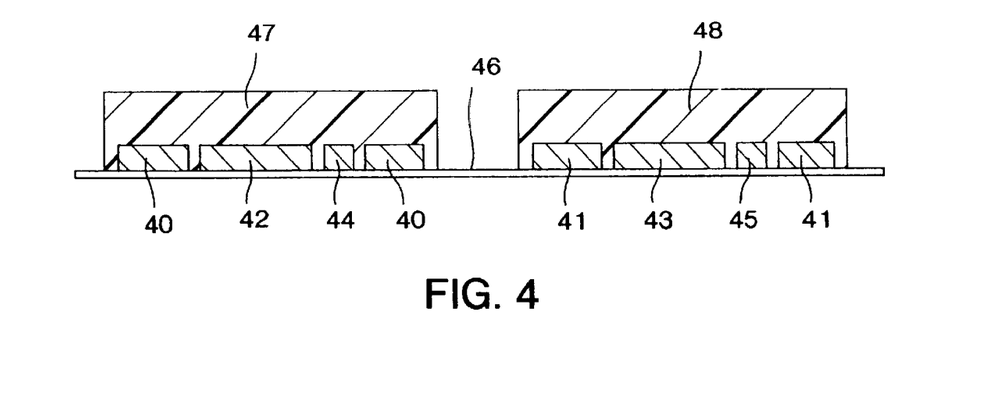
FIG. 4 is a representation of a cross-sectional schematic view of the bimodal electrodes as they may be used in conjunction with a reference electrode and a hydrogel pad. In the figure, the components are as follows: bimodal electrodes 40 and 41; sensing electrodes 42 and 43; reference electrodes 44 and 45; a substrate 46; and hydrogel pads 47 and 48.

In an alternative embodiment, the sampling device can operate in an alternating polarity mode necessitating the presence of a first and second bimodal electrodes (FIG. 4, 40 and 41) and two collection reservoirs (FIG. 4, 47 and 48). Each bi-modal electrode (FIG. 3, 30; FIG. 4, 40 and 41) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode at which the chemical compound is catalytically converted at the face of the sensing electrode to produce an electrical signal.

The reference (FIG. 4, 44 and 45; FIG. 3, 32) and sensing electrodes (FIG. 4, 42 and 43; FIG. 3, 31), as well as, the bimodal electrode (FIG. 4, 40 and 41; FIG. 3, 30) are connected to a standard potentiostat circuit during sensing. In general, practical limitations of the system require that the bimodal electrode will not act as both a counter and iontophoretic electrode simultaneously.

The general operation of an iontophoretic sampling system is the cyclical repetition of two phases: (1) a reverse-iontophoretic phase, followed by a (2) sensing phase. During the reverse iontophoretic phase, the first bimodal electrode (FIG. 4, 40) acts as an iontophoretic cathode and the second bimodal electrode (FIG. 4, 41) acts as an iontophoretic anode to complete the circuit. Analyte is collected in the reservoirs, for example, a hydrogel (FIG. 4, 47 and 48). At the end of the reverse iontophoretic phase, the iontophoretic current is turned off. During the sensing phase, in the case of glucose, a potential is applied between the reference electrode (FIG. 4, 44) and the sensing electrode (FIG. 4, 42). The chemical signal reacts catalytically on the catalytic face of the first sensing electrode (FIG. 4, 42) producing an electrical current, while the first bi-modal electrode (FIG. 4, 40) acts as a counter electrode to complete the electrical circuit.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode must not limit the speed of the reaction at the sensing electrode. In the case of a large sensing electrode, the ability of the counter electrode to source proportionately larger currents is required.

The design of the sampling system provides for a larger sensing electrode (see for example, FIG. 3) than previously designed. Consequently, the size of the bimodal electrode must be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present sampling system, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present sampling system are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Since the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the sampling system described herein, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$, preferably about 0.85 $cm^2$. These electrodes provide for reproducible, repeated cycles of charge passage at current densities ranging from about 0.01 to 1.0 $mA/cm^2$ of electrode area. More particularly, electrodes constructed according to the above formulation parameters, and having an approximate electrode area of 0.85 $cm^2$, are capable of a reproducible total charge passage (in both anodic and cathodic directions) of 270 mC, at a current of about 0.3 mA (current density of 0.35 $mA/cm^2$) for 48 cycles in a 24 hour period.

Once formulated, the Ag/AgCl electrode composition is affixed to a suitable rigid or flexible nonconductive surface as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate. This low temperature screen print can be carried out at about 125 to 160° C., and the screening can be carried out using a suitable mesh, ranging from about 100–400 mesh.

In another preferred embodiment, the automatic sampling system transdermally extracts the sample in a continual manner over the course of a 1–24 hour period, or longer, using sonophoresis. More particularly, a source of ultrasonic radiation is coupled to the collection reservoir and used to provide sufficient perturbation of the target tissue surface to allow passage of the analyte (glucose) across the tissue surface. The source of ultrasonic radiation provides ultrasound frequencies of greater than about 10 MHz, preferably in the range of about 10 to 50 MHz, most preferably in the range of about 15 to 25 MHz. It should be emphasized that these ranges are intended to be merely illustrative of the preferred embodiment; in some cases higher or lower frequencies may be used.

The ultrasound may be pulsed or continuous, but is preferably continuous when lower frequencies are used. At very high frequencies, pulsed application will generally be preferred so as to enable dissipation of generated heat. The preferred intensity of the applied ultrasound is less than about 5.0 $W/cm^2$, more preferably is in the range of about 0.01 to 5.0 $W/cm^2$, and most preferably is in the range of 0.05 to 3.0 $W/cm^2$.

Virtually any type of device may be used to administer the ultrasound, providing that the device is capable of producing the suitable frequency ultrasonic waves required by the sampling system. An ultrasound device will typically have a power source such as a small battery, a transducer, and a means to attach the system to the sampling system collection reservoir. Suitable sonophoresis sampling systems are described in International Publication No. WO 91/12772, published Sep. 5, 1991, the disclosure of which is incorporated herein by reference.

As ultrasound does not transmit well in air, a liquid medium is generally needed in the collection reservoir to efficiently and rapidly transmit ultrasound between the ultrasound applicator and the tissue surface.

Figure 2:
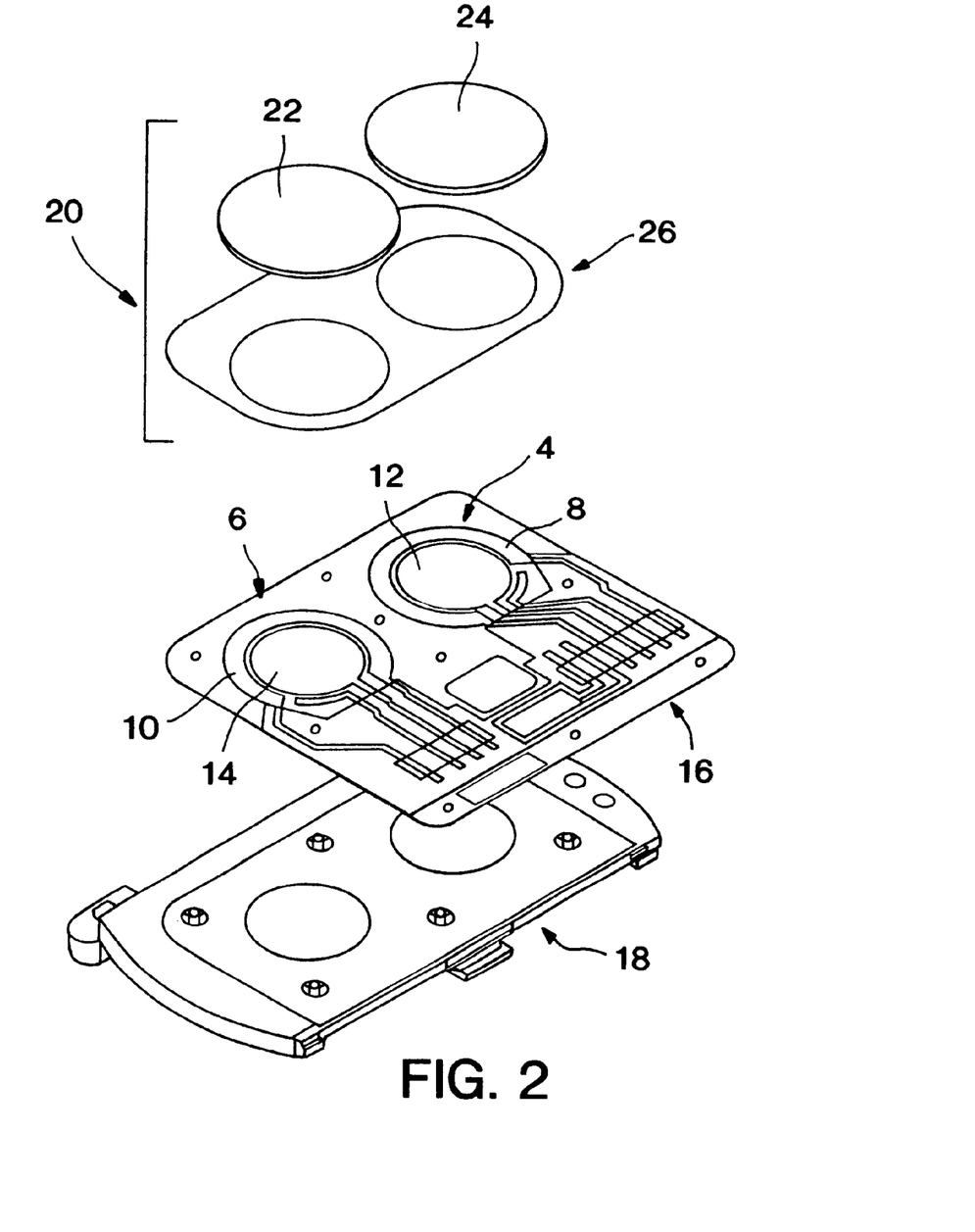
FIG. 2 is an exploded pictorial representation of components from a preferred embodiment of the automatic sampling system of the present invention.

Referring now to FIG. 2, an exploded view of the key components from a preferred embodiment of an iontophoretic sampling system is presented. The sampling system components include two biosensor/iontophoretic electrode assemblies, 4 and 6, each of which have an annular iontophoretic electrode, respectively indicated at 8 and 10, which encircles a biosensor 12 and 14. The electrode assemblies 4 and 6 are printed onto a polymeric substrate 16 which is maintained within a sensor tray 18. A collection reservoir assembly 20 is arranged over the electrode assemblies, wherein the collection reservoir assembly comprises two hydrogel inserts 22 and 24 retained by a gel retainer 26.

Figure 7:
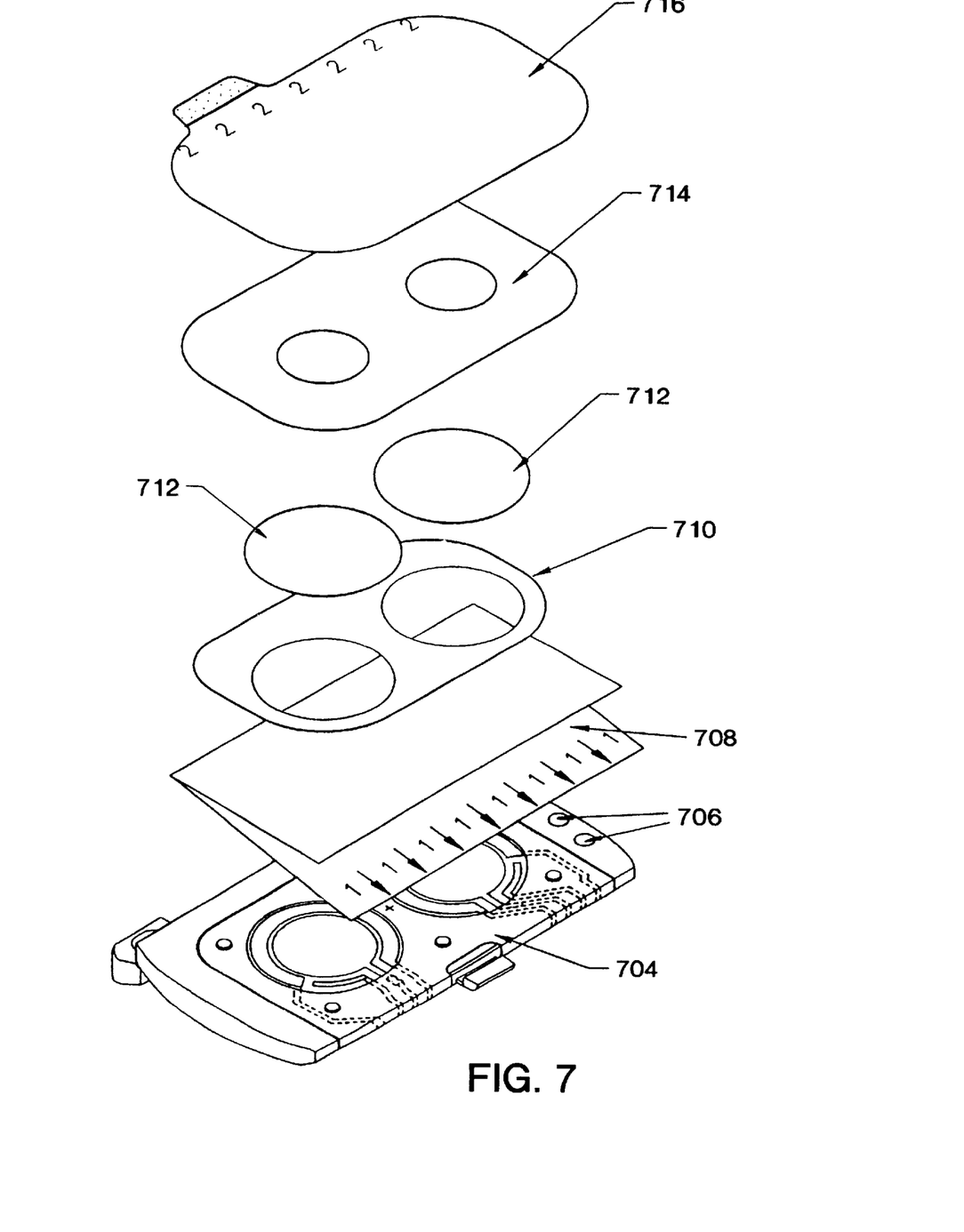
FIG. 7 depicts an exploded view of another embodiment of a gel/sensor-containing collection assembly for use in an iontophoretic sampling system.

Referring now to FIG. 7, an exploded view of the key components from another embodiment of an iontophoretic sampling system is presented. The sampling system components include, but are not limited to, the following: a sensor-to-tray assembly comprising two bimodal electrode assemblies and a support tray 704; two holes 706 to insure proper alignment of the support tray in the sampling device (e.g., these holes are aligned with corresponding pegs in the sample device; similar holes in the flanged surface of the present invention (which do not interfere with the cover's ability to retain fluids) may also serve to provide proper alignment for the cover of the present invention); a plowfold liner 708 used to separate the sensors from the hydrogels 712 (for example, during storage); a gel retaining layer 710; a mask layer 714 (where the gel retaining layer, hydrogels, and mask layer form a collection assembly, which can, for example, be a laminate); and a patient liner 716. When such an assembly is in use in a sampling device the liners (708 and 716) are removed.

In one embodiment, the electrode assemblies can include bimodal electrodes as shown in FIG. 3 and described above.

The components shown in exploded view in FIGS. 2 and 7 are each intended for use in a automatic sampling device which is configured to be worn like an ordinary wristwatch. As described in International Publication No. WO 96/00110, published Jan. 4, 1996, the wristwatch housing (not shown) contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Modifications and additions to the embodiments of FIGS. 2 and 7 will be apparent to those skilled in the art.

3. Quality Control Testing Kits and Methods of Use Thereof

The above-described automatic sampling device, which is configured to be worn like an ordinary wristwatch, uses a replaceable component that includes hydrogel inserts. In one embodiment, the sampling system shown in FIG. 2 comprises such a replaceable component. Each time the sampling system is replaced it is tested to insure that it will respond in a predictable way to a known concentration of glucose. Such quality control testing is important in the above-described device because the hydrogel can contain analyte-specific enzyme systems that are sensitive to storage, processing, and/or shipping conditions.

For example, in one embodiment described above, the hydrogel contains glucose oxidase which oxidizes glucose to gluconic acid and hydrogen peroxide. Glucose oxidase is sensitive to temperatures above 40°. When the replaceable sampling system is manufactured and shipped to an end-user (subject) the functionality of the sampling system should be verified to insure optimal performance of the system. Typically the replaceable sampling system is manufactured in batches or lots and representatives of each batch or lot can be tested. The kit and method of the present invention provide means for such quality control testing of the replaceable component of the sampling system.

In one embodiment, after assembly of the replaceable sampling system (such as is shown in FIG. 2) with the housing unit, the surface of the sampling system having a reservoir containing an ionically conductive medium is exposed. A solution containing a known amount of the analyte of interest can be layered onto this surface in sufficient quantity to cover the ionically conductive medium, for example, hydrogel pads. A quality control test is then run by the sampling device. In the case of glucose, the analyte (glucose) reacts with the glucose oxidase within the hydrogel to produce hydrogen peroxide. The presence of hydrogen peroxide generates a current at the biosensor electrode that is directly proportional to the amount of hydrogen peroxide in the reservoir. This current provides a signal which can be detected and is then interpreted by an associated system controller to determine the sensitivity of the detection system relative to the glucose concentration e.g., see Example 1). Because the glucose concentration of the test solution is known, measurements obtained by the sampling system can be correlated to actual values using known statistical techniques. The end-user then determines whether the test value for the sampling system falls within an acceptable, specified range that indicates the efficacy and usefulness of the replaceable sampling system. An acceptable range, for example, percent error bracketing the test value, is determined and provided by the manufacturer of the sampling system. Typically, for a test solution of 100 $\mu$M glucose an acceptable range for the error is plus-or-minus about 50%, preferably plus-or-minus about 30%.

In another aspect of the present invention, a pad can be used to contain the analyte solution. The pad can be composed of any suitable material that allows the analyte to come into contact with the ionically conductive medium. Exemplary materials include, but are not limited to, non-woven Rayon, cellulose acetate, polycarbonate, crosslinked polyethylene oxide, polyethylene, and polyester. In one embodiment, the pad is composed of cellulose acetate, and saturated with a solution of 100 $\mu$M glucose. The solution may also contain preservatives. The glucose solution should be stable in that the concentration of glucose should remain constant, that is, conditions that potentially lead to the breakdown or modification of glucose should be avoided (for example, bacterial contamination). Such pads may, for example, be individually packaged in foil pouches.

In yet another aspect of the present invention, a test well can be formed having sides and a membrane-sealed bottom. The test well is placed in contact with the ionically conductive medium and the test solution is placed in the test well. The analyte is capable of crossing the membrane by diffusion. Alternately, the test well may be a sealed unit having a top, sides, and a membrane-sealed bottom, where the test well is filled with an appropriate test solution. The membrane bottom of the well can be protected and sealed by, for example, an adhered foil cover that can be removed (e.g., peeled off) before use of the test well. The test well can be made of any suitable material, including, but not limited to, polystyrene, polyester glycol, and sheet vinyl. Suitable membranes can be obtained from a variety of sources including, but not limited to, Pierce (Rockford, Ill.), Spectrum Medical (Laguna Hills, Calif.), Whatman (Tewksbury, Md.), and Gelman Sciences (Ann Arbor, Mich.). Also, delivery of the analyte of the test solution to the ionically conductive medium may be regulated by the membrane by varying, for example, pore size and/or thickness of membrane, both of which control analyte diffusion.

A preferred method of performing the quality control test of the present invention is as follows. An iontophoretic sampling system, having first and second surfaces, is assembled into an appropriate housing. The housing can include suitable electronics (e.g., microprocessor, memory, display and other circuit components) and power sources for operating the automatic sampling system. The second surface makes the required connections/contacts with the housing unit to, for example, supply power. The first surface has a reservoir containing an ionically conductive medium, and, for example, in the case of glucose, an enzyme capable of reacting with glucose to produce hydrogen peroxide.

A cover is placed on the first surface of the iontophoretic sampling system, where the cover has a shape that encloses the reservoirs containing the ionically conductive medium. The cover typically has a top and sides, such that when the cover is in contact with the first surface of the iontophoretic sampling system the first surface creates a bottom for the cover resulting in an enclosed space (or "test well"). The cover adheres to the first surface such that when fluid is introduced into the enclosed space there is no leakage. An adhesive can be present on the parts of the top that contact the first surface of the sampling system. Alternately, enough adhesive is typically present on the first surface of the sampling system to securely hold the top in place—such adhesive is often supplied on the first surface of the sampling system to insure efficacious contact of the ionically conductive medium with a subject's skin. The top of the cover typically has an opening in through which a glucose solution can be introduced. In addition, the top of the cover may have a small hole or slit, or a series of small holes or slits, to allow air to escape from the enclosed space when the liquid is introduced.

A stable solution of glucose is then introduced through the opening in a sufficient volume to cover the ionically conductive medium, and usually to fill the enclosed space. Elimination of air bubbles, particularly on the surface of the ionically conductive medium, is desirable. An adhesive seal may be used to cover the opening and any other holes or slits, in order to prevent spilling the solution. Such a seal is particularly useful to protect sensitive electronic components in the housing unit from coming into contact with the analyte test solution.

The sampling system is then activated to test the iontophoretic sampling system's sensitivity relative to a concentration of glucose in a glucose solution (e.g., see Example 1). A value is typically determined that is related to the concentration of glucose in the test solution. As discussed above, because the glucose concentration of the test solution is known, measurements obtained by the sampling system can be correlated to actual values using known statistical techniques.

One embodiment of such a cover is shown in FIGS. 5A, 5B, and 5C. The cover can be made, for example, of polyester glycol. In FIG. 5A, a top view of the cover is displayed along with dimensions in inches. The top view illustrates the dimensions for width (1.150 inches) and length (1.950 inches) of the cover, as well as, other measurements in inches. The number "2" enclosed in a triangle indicates a "slit" in the top of the cover. FIG. 5B shows a side view of the cover. From this view the depth of the well (0.170 inches) and angle (60°) are defined. Units are in inches. The cover as shown in FIG. 5C can be placed over the ionically conductive medium (e.g., hydrogel inserts 22 and 24, FIG. 2) of the sampling system.

Such covers can be formed by, for example, the following methods: thermal forming, injection molding, vacuum forming, and pressure forming. Materials suitable for use in such covers include, but are not limited to, polystyrene, polycarbonate, nylon, and polyester glycol. Generally the cover is clear or lightly tinted to allow the user (subject) to see whether air bubbles are present within the enclosed space.

The analyte solution can be prepared in a variety of ways to provide a stable solution of known analyte concentration. In the case of glucose, the solution is typically 100 $\mu$M ±10%, with a preferred concentration of 100 $\mu$M. Some guidelines for the preparation of the solution are discussed below. The solution should be stable in that the concentration of glucose should remain constant before use, that is, conditions that potentially lead to the breakdown or modification of glucose should be avoided (for example, bacterial contamination). The solution may also be preserved with a substance that stabilizes the solution (for example, by preventing bacterial growth) but that does not interfere with detection of the analyte by the sampling system. Such preservatives include, but are not limited to, sodium benzoate [e.g., 0.2% (w/w)], Nipastat® (including, methyl propyl isoparaben), sodium azide, and sodium nipagin.

The analyte solution is generally packaged in individual containers having sufficient volume for a single quality control test, i.e., a volume that will at least cover the ionically conductive medium and preferably fill the enclosed space formed by contact of the cover with the sampling means. Relative to the cover shown in FIGS. 5A, 5B, and 5C such a volume is approximately 2.0 mls. to approximately 2.5 mls.

Manufacturing of the glucose solution will generally adhere to the following requirements. The bottle and solution components are handled and stored in such a manner to minimize the risk of particulate and microbial contamination of the product. Typical microbial limits for the solution are as follows: total aerobic microbial count less than 100 CFU/ml; and, contained yeast and mold count less than 10 CFU/ml. The glucose solution should, for example, test negative for Staphylococcus and Pseudomonas. The glucose solution and filled receptacles (containers) are stored in a normal room temperature environment. The containers typically have instructions or indications printed on them. Filling and any such printing can be carried out in a HEPA-filtered or laminar-flow environment. The printing and filling equipment must be sufficiently sanitized. The resulting product is inspected to assure container seal integrity and fill-volume requirements.

Any number of suitable containers can be chosen for the glucose solution. Containers are typically formed by blow molding or injection molding. Materials the containers can be made of include, but are not limited to, polypropylene, and polyethylene. An exemplary snap-top container for a quality control test glucose solution is shown in FIG. 6. In the figure, the dimensions of the container (i.e., height (3.12 inches), width (1.06 inches) are shown. Locations of associated text are indicated in the figure as well.

The present invention includes kits useful for practicing the quality control testing method of the present invention. Such kits can include, but are not limited to, the following components: a cover (or test well); an analyte solution; an adhesive strip to seal the test well after introduction of the analyte solution; and instructions for use.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (e.g., glucose) to the extent that a product of this reaction can be sensed, e.g., can be detected electrochemically from the generation of a current which current is detectable and proportional to the concentration or amount of the analyte which is reacted. One suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxidase-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

In the case of such systems appropriate formulations of analyte test solutions can be employed. For example, test solutions having known concentrations of alcohol, uric acid, cholesterol, or theophylline. The solutions may contain additives, diluents, solubilizers, and the like, that do not interfere with detection of the analyte of interest by the sampling system.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

All patents, patent applications, and publications mentioned herein, both supra and infra, are hereby incorporated by reference.

EXAMPLE 1

Quality Testing of a Glucose Sampling System

Exemplary Quality Control (QC) Testing was carried out using (1) a sampling system similar to that described above and shown in FIG. 2, (2) a cover essentially as shown in FIG. 5C, and (3) a 100 $\mu$M glucose test solution. The cover was placed on the sampling system and the test well was filled with the glucose solution. Air bubbles were eliminated.

Eighty biosensor measurements were taken every 5 seconds for a biosensor period from 43 minutes to 50 minutes elapsed time (ET) from the start of the QC Test. These readings were processed to give a "QC Result" or QC using the following equation for finding QC:

$$QC = \frac{\sum_{j=1}^{80}(i_A+i_b)_j}{1000} \times QC_{factor} \quad (1)$$

where: QC, quality control value; j, the number of biosensor measurements; $i_A$, current at a first sensor; $i_B$, current at a second sensor; and $QC_{factor}$, which was found experimentally to be 1/7 or 0.14286. Further, where the relationship of charge (Q), current (i), and time (t) was essentially as follows, for the calculation of the total charge on the first and second sensors:

$$Q = \sum_{j=1}^{80}(i_A+i_B)_j \Delta t \quad (2)$$

Based on a series of experiments performed in support of the present invention, the QC Test method gave results averaging around 350,000 nano-Coulombs (nC) for a 100 $\mu$M glucose solution. This value was converted to a "QC Result" (QC) of 20 (presented with a decimal point in the below data—i.e., a "2.0").

The Quality Control test was repeated on several lots of sampling means and the results are presented in Table 1.

TABLE 1

| Lot # | 00358 | 00368 | 00388 | 00498 |
|---|---|---|---|---|
| QC Reading | 2.2 ± + 0.1 | 2.0 ± 0.1 | 2.1 ± 0.1 | 2.2 ± 0.1 |

For the Quality Control Tests: a new cover was used for each test with each new sampling means, and 100 $\mu$M glucose in 0.2% sodium benzoate solution was used for the test. QC reading was set to 2.0 when the sensor charge was 35,000 nC.

These results demonstrate the usefulness and efficacy of the quality control test kit and methods of the present invention.

Although preferred embodiments of the subject invention have been described in some detail, it is understood that obvious variations can be made without departing from the spirit and the scope of the invention as defined by the appended claims.

What is claimed is:

1. A kit for testing the efficacy of a glucose monitoring system, said monitoring system comprising an iontophoretic sampling system and a sensor element wherein said iontophoretic sampling system comprises a first surface, said first surface comprising a reservoir, said reservoir comprising an ionically conductive medium and an enzyme capable of reacting with glucose to produce hydrogen peroxide, said kit comprising:

a cover having a shape that encloses said reservoir when said cover is placed in contact with said first surface of the iontophoretic sampling system said cover having a tops surface, retaining sides, and a bottom surface wherein (i) the bottom surface defines an opening, and (ii) when the bottom surface of the cover is in contact with the first surface of the iontophoretic sampling system, said first surface completes a bottom for said cover creating an enclosed space, and further wherein the top of said cover defines an opening through which a solution can be introduced into said enclosed space, and a container holding a stable solution of glucose having a known concentration of glucose, wherein said glucose solution has a volume sufficient to at least cover said ionically conductive medium when it is introduced into said enclosed space.

2. The kit of claim 1, wherein said cover is formed from a material selected from the group consisting of polystyrene, polycarbonate, nylon, and polyester glycol.

3. The kit of claim 1, wherein said cover further defines a slit centrally located in the top of the cover.

4. The kit of claim 3, further comprising an adhesive strip effective to seal said opening and said slit.

5. The kit of claim 1, wherein said bottom surface of said cover is a flanged surface.

6. The kit of claim 1, wherein said bottom surface of said cover has an adhesive distributed thereon.

7. The kit of claim 1, further comprising instructions for use.

8. The kit of claim 1, wherein said glucose solution has a concentration of 100 $\mu$M.

9. The kit of claim 1, wherein said glucose solution further comprises a preservative.

10. The kit of claim 9, wherein said preservative is selected from the group consisting of sodium benzoate, methyl prophyl isoparaben, sodium azido, and sodium nipagin.

11. The kit of claim 10, wherein the preservative comprises sodium benzoate at 0.2% (w/w).

12. The kit of claim 1, wherein said container is a snap-top container.

13. A method of testing a glucose monitoring system to determine the sensitivity of the monitoring system relative to a known concentration of glucose in a glucose solution, said monitoring system comprising, an iontophoretic sampling system and a sensing element, said iontophoretic sampling system comprising a first surface, said first surface comprising a reservoir, said reservoir comprising an ionically conductive medium and an enzyme capable of reacting with glucose to produce hydrogen peroxide, said method comprising:

placing a cover in contact with said first surface of the iontophoretic sampling system, said cover having a top surface, retaining sides, and a bottom surface wherein (i) the bottom surface defines an opening, and (ii) when the bottom surface of the cover is in contact with the first surface of the iontophoretic sampling system, said first surface completes a bottom for said cover creating an enclosed space, and further wherein the top of said cover defines an opening through which a solution can be introduced into said enclosed space, introducing a solution of glucose having a known concentration of glucose through said opening into said enclosed space, wherein said glucose solution has a volume sufficient to at least cover said ionically conductive medium; and testing the glucose monitoring system's sensitivity relative to the known concentration of glucose in the glucose solution.

14. A method of testing a glucose monitoring system's ability to determine a known concentration of glucose in a glucose solution, said monitoring system comprising, an iontophoretic sampling system and a sensing element, said iontophoretic sampling system comprising a first surface, said first surface comprising a reservoir, said reservoir comprising and ionically conductive medium and an enzyme capable of reacting with glucose to produce hydrogen peroxide, said method comprising:

placing a cover in contact with said first surface of the iontophoretic sampling system, said cover having a top surface, retaining sides, and a bottom surface wherein (i) the bottom surface defines an opening, and (ii) when the bottom surface of the cover is in contact with the first surface of the iontophoretic sampling system, said first surface completes a bottom for said cover creating an enclosed space, and further wherein the top of said cover defines and opening through which a solution can be introduced into said enclosed space, introducing a solution of glucose having a known concentration of glucose through said opening into said enclosed space, wherein said glucose solution has a volume sufficient to at least cover said ionically conductive medium; and testing the glucose monitoring system's ability to determine the known concentration of glucose in the glucose solution.

15. A method of testing monitoring system to determine that the glucose monitoring system can provide a predicable response to a known concentration of glucose in a glucose solution, said monitoring system comprising, an iontophoretic sampling system and a sensing element, said iontophoretic sampling system comprising a first surface, said first surface comprising a reservoir, said reservoir comprising an ionically conductive medium and a enzyme capable of reacting with glucose to produce hydrogen peroxide, said method comprising:

placing a cover in contact with said first surface of the iontophoretic sampling system, said cover having a top surface, retaining sides, and a bottom surfaces wherein (i) the bottom surface of the cover is in contact with the first surface of the iontophoretic sampling system, said first surface completes a bottom for said cover creating and enclosed space, and further wherein the top of said cover defines and opening through which a solution can be introduced into said enclosed space, introducing a solution of glucose having a known concentration of glucose through said opening into said enclosed space, wherein said glucose solution has a volume sufficient to at least cover said ionically conductive medium; and testing the glucose monitoring system's ability to provide a predictable response to the known concentration of glucose in the glucose solution.

\* \* \* \* \*

UNITED STATES PATENT AND TRADEMARK OFFICE
CERTIFICATE OF CORRECTION

PATENT NO. : 6,391,643 B1  Page 1 of 1
DATED : May 21, 2002
INVENTOR(S) : Qiang Chen et al.

It is certified that error appears in the above-identified patent and that said Letters Patent is hereby corrected as shown below:

<u>Title page,</u>
Item [54], Title "KIT AND METHOD FOR QUALITY CONTROL TESTING OF AN IONTOPHORETIC SAMPLING SYSTEM" should be -- KIT AND METHOD FOR QUALITY CONTROL TESTING OF A GLUCOSE MONITORING SYSTEM --;

<u>Column 22,</u>
Line 59, "tops surface," should be -- top surface --;

<u>Column 23,</u>
Line 25, "sodium azido," should be -- sodium azide --

<u>Column 24,</u>
Line 30, "testing monitoring system" should be -- testing a glucose monitoring system --;
Line 37, "and a enzyme" should be -- and an enzyme --; and
Line 42, "a bottom surfaces wherein (i) the bottom surface of the cover is in contact" should be -- a bottom surface wherein (i) the bottom surface defines an opening, and (ii) when the bottom surface of the cover is in contact --

Signed and Sealed this

First Day of October, 2002

Attest:

Attesting Officer

JAMES E. ROGAN
*Director of the United States Patent and Trademark Office*